United States Patent [19]

Lemelson

[11] 4,270,536
[45] Jun. 2, 1981

[54] DISPOSABLE SYRINGE

[76] Inventor: Jerome H. Lemelson, 85 Rector St., Metuchen, N.J. 08840

[21] Appl. No.: 80,562

[22] Filed: Oct. 1, 1979

[51] Int. Cl.³ .............................................. A61M 5/00
[52] U.S. Cl. ................................. 128/218 N; 128/221
[58] Field of Search ........ 128/218 R, 218 P, 218 DA, 128/218 N, 221, 215, 216

[56] References Cited

U.S. PATENT DOCUMENTS

| | | | |
|---|---|---|---|
| 1,139,368 | 5/1915 | Pierce | 128/218 P |
| 2,693,803 | 11/1954 | Ogle | 128/218 P |
| 2,832,340 | 4/1958 | Dann et al. | 128/218 P |
| 3,943,926 | 3/1976 | Barragan | 128/218 DA |

Primary Examiner—John D. Yasko

[57] ABSTRACT

A disposable hypodermic syringe is provided which contains storage and breakage means for the needle of the syringe to prevent the needle from causing injury, damage or infection to a person handling the syringe or garbage containing the syringe after it is used and disposed of. In one form, the piston of the syringe is molded with an elongated cavity in its end, into which cavity the needle of the syringe may be inserted and broken off the needle receptacle. The cavity may be such as to frictionally retain the end of the needle therein to facilitate breakage and prevent its removal. In another form, the mount for the needle is constructed to facilitate breakage and to retain the broken needle in the cavity receptacle.

6 Claims, 9 Drawing Figures

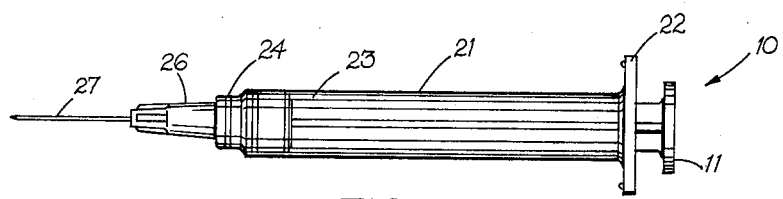
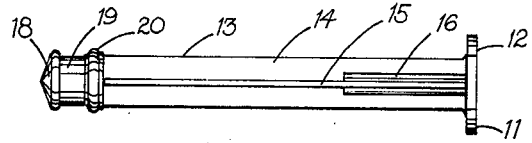
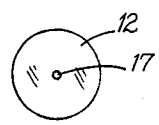
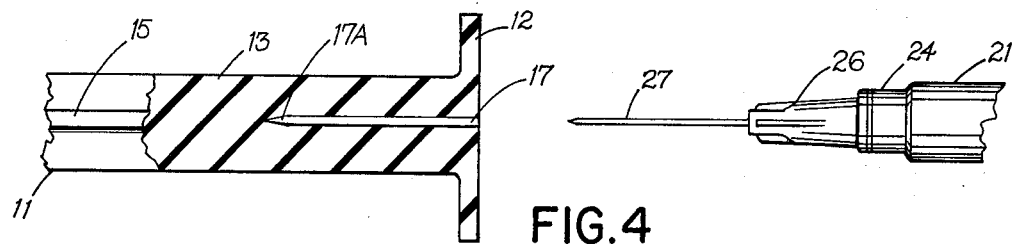
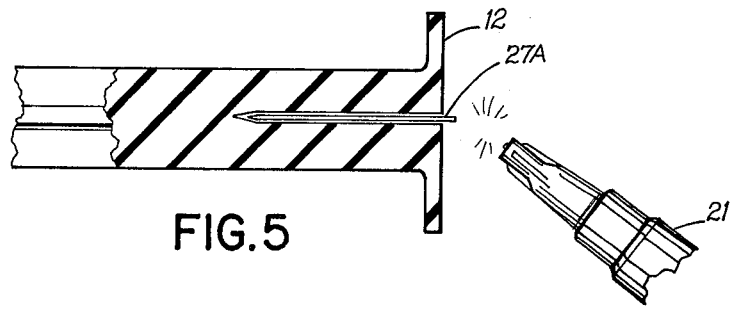
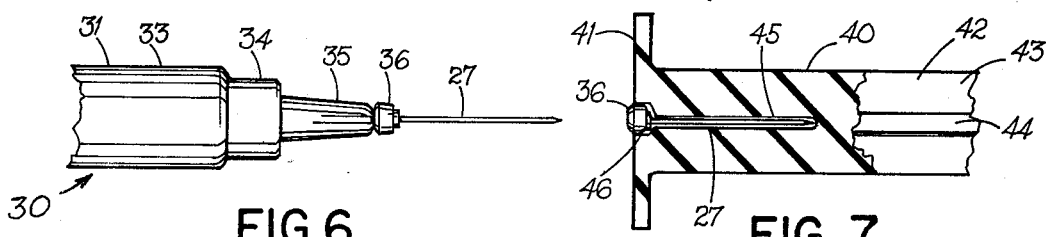
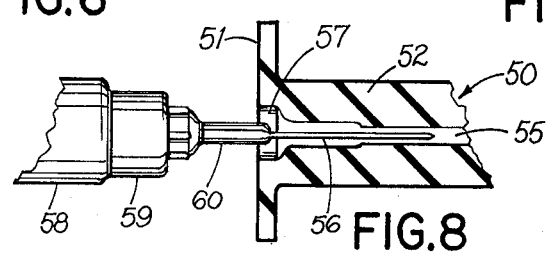
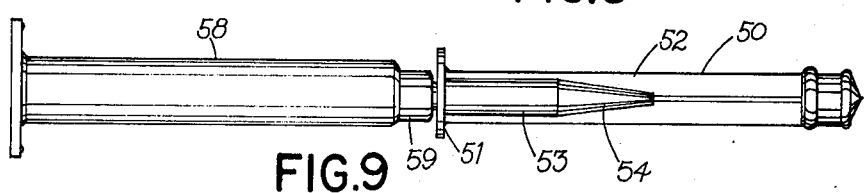

DISPOSABLE SYRINGE

SUMMARY OF THE INVENTION

This invention relates to a disposable hypodermic syringe which is constructed of a plurality of components, one of which contains an elongated cavity or hole for receiving the needle of the syringe and retaining it therein after it is broken off its mount.

It is known in the art to fabricate hypodermic syringes of molded plastic, which contains a main body of tubular shape having a needle secured to an end thereof and a cylinder for receiving the end of a piston plunger for forcing liquid medication from the chamber through the needle into tissue of a person or animal. A prime problem encountered in such a disposable syringe is that the needle, when attached to the end of the cylinder, poses a hazard to persons handling the syringe after it has been used and, as such, may cause infection or injury to such person.

Accordingly, it is a primary object of this invention to provide a new and improved disposable hypodermic syringe with means for receiving, facilitating breakage of the needle and retaining the broken needle so that it will not pose a hazard thereafter.

Another object is to provide a hypodermic syringe with a plunger portion which is shaped to receive and retain the needle of the syringe after it has been used and to facilitate breakage of such needle from the main body of the syringe.

Another object is to provide a hypodermic syringe containing a needle which is specially constructed to facilitate its breakage so that it may be disposed safely.

With the above and such other objects in view as will hereafter more fully appear, the invention consists of the novel constructions, combinations and arrangements of parts illustrated in the drawings and described in the accompanying specifications, but it is to be understood that changes, variations and modifications may be resorted to which come within the purview of the invention without departing from the spirit and nature of the invention.

In the drawings:

FIG. 1 is a side view of a hypodermic needle assembly.

FIG. 2 is a side view of the plunger portion of the hypodermic needle assembly of FIG. 1 containing a receptacle for the needle of the cylinder portion.

FIG. 3 is an end view of FIG. 2.

FIG. 4 is a side view of a portion of the end of the plunger of FIG. 2 in cross section to indicate a receptacle formed therein.

FIG. 5 shows the needle of the cylinder of FIG. 4 inserted into the receptacle in the head of the plunger and broken off.

FIG. 6 is a side view of a portion of the end of a syringe housing and needle containing a special molded portion at its end for facilitating breakage of the needle and its retention in the head of the plunger of the syringe.

FIG. 7 is a side view of a fragment of the end of the plunger and the syringe of FIG. 6, cross sectioned to show the broken needle and receptacle therefor.

FIG. 8 is a fragmentary view of the end of the syringe and the plunger therefor, which is illustrated in the cross section, showing specially shaped needle and retainer being inserted into a receptacle, and FIG. 9 is a side view of the syringe of FIG. 8 and a needle thereof retained within the plunger portion of the syringe.

FIG. 1 illustrates a disposable hypodermic syringe assembly 10 comprising a plunger unit 11 and a cylinder unit 21 having a cylindrical tubular side wall 23, and a retaining portion 26 for a hypodermic needle 27 at the far end 24 of the cylinder 21. The cylinder 21 and plunger 11 are preferably molded of plastic forming a low cost disposable assembly.

As shown in FIG. 2, the plunger 11 has a head 12 integrally molded with an elongated shank 13 formed of respective rib-like formations 14 and 15 which extend at right angles to each other substantially the length of the shank 13. At the far end of the shank 13 is molded a piston 18 having a cylindrical side wall 19 and a resilient ring-like formation 20 which is compressed in the piston portion 18 and inserted into the open end of the cylinder 21 so as to provide a circumscribing seal between the piston portion and the inside walls of the cylinder 21. Thus, as the head 12 is pushed to force the piston portion 18 through the cylinder 21, liquid contained in the volume between the piston and cylinder is forced forwardly and through the hollow hypodermic needle 27 to be expelled from the open end thereof.

Molded as part of the head end of the plunger 11 is a cylindrical formation 16 extending between the rib-like formations 14 and 15 which, as shown in FIG. 3, provides an open elongated cavity 17 extending most of the distance through the formation 16.

As shown in FIG. 4, after the syringe has been used and is ready to be disposed of, the plunger part 11 is removed from the cylinder and the head portion 12 is disposed in front of the hypodermic needle 27 of the cylinder assembly 21 permitting the needle to be inserted into the elongated hole or cavity 17 which is molded through the head 12 and the cylindrical portion 16 of the plunger. The forward end 17A of the cavity 17 is tapered to frictionally receive and retain the needle 27 which may be broken off from its mount 26 at the end of the cylinder 21, as shown in FIG. 5, by deflecting the cylinder assembly and the plunger assembly 11 until the needle snaps or breaks, as illustrated, leaving the major portion 27A of the needle frictionally retained within the cavity 17.

To facilitate breakage of the needle 27, the side wall thereof immediately adjacent the end of the retaining portion 26 of the cylinder 21, may be nicked or ground with an indentation such that, upon bending the needle with respect to the cylinder 21, it will break off as shown. The pointed end of the needle portion 27A may actually penetrate beyond the tapered end portion 17A of the cavity 17 to better frictionally retain the needle within the cavity and facilitate breakage.

In FIG. 6, the cylinder 31 of a hypodermic syringe has its cylindrical side wall 33 formed at its end portion 34 with a tapered solid retaining portion 35 for the hypodermic needle 27 which extends through section 35 to the interior of the cylinder for receiving a liquid to be ejected from the needle 27. The end 36 of the retaining portion 35 of the hypodermic cylinder 33 is formed, as shown, as a tapered disc-like formation which is configured to be frictionally retained within a sub-cavity 46 extending to the main elongated cavity 45 which is formed in and extends through the center of the plunger 40 for a hypodermic syringe 30 of which the cylinder assembly 31 forms a part. The plunger 40 contains an integrally molded head 41 which may be gripped by the thumb of the user to force the plunger through the cylinder 33. The shank 42 of the plunger 40 is formed of rib-like formations 42 and 44 which extend at right angles to each other, although such shank may also be a solid cylinder. Once the needle 27 is inserted into the elongated cavity or hole 45 molded in the head 41 in the end portion of the plunger 40, it may be retained therein by means of a frictional fit between the exterior surface of the formation 36 and the wall of the sub-cavity 46 molded in the plunger portion 40.

In FIGS. 8 and 9, the plunger 50 is formed with a head 51 and a shank 52 and contains an elongated hole or cavity 55 extending partially through the plunger from the head 51 with a sub-cavity 56 of greater diameter than the diameter of the main portion of the cavity 55 for receiving and retaining a protruding portion 60 of the end 59 of the cylinder 58 of a hypodermic syringe. The formation 60 serves to support the end of the needle 56 which is not broken off when the syringe is disposed but is retained within the hole or cavity portions 55 and 56, as shown in FIG. 8, which are centrally formed in cylindrical and conical formations 53 and 54 provided near the head end of the plunger 50. The assembly illustrated in FIG. 9 in which the needle and formation 60 are respectively gripped and retained within the cavity portions 55 and 56, to retain the components assembled as shown when disposed of, provide a suitable means for preventing the needle 56 from injuring or infecting a person's hand, without the need to break the needle from the cylinder 58.

I claim:
1. A hypodermic syringe comprising in combination:
   a syringe cylinder which is open at one end and closed at the other,
   a hypodermic needle secured to the closed end of the cylinder and communicating with its interior for receiving a liquid forced through the cylinder,
   piston means, including an elongated shank for supporting said piston means, and slidably supported within said cylinder,
   the end of said shank opposite said piston means having an increased diameter portion permitting it to be engaged by the thumb of a hand of a person utilizing said syringe,
   an elongated cavity formed in the central portion of said increased diameter portion and extending into said shank
   said elongated cavity being of sufficient depth to receive substantially the entire portion of said hypodermic needle protruding from the end of the syringe cylinder and of such a diameter as to retain said needle against lateral displacement therein of a degree which would prevent the breakage of said needle so as to permit the bending and breaking of said needle while disposed within said cavity.

2. A hypodermic syringe in accordance with claim 1 in which the wall of said cavity is shaped to frictionally hold a needle therein when the needle is fully inserted into the cavity and is broken off the end of said cylinder.

3. A hypodermic syringe in accordance with claim 1 wherein the end of said elongated cavity is tapered and shaped to frictionally engage the end of the hypodermic needle inserted into the cavity while attached to said hypodermic cylinder.

4. A hypodermic syringe in accordance with claim 1 wherein said shank is formed of a plastic capable of being penetrated by the end of a hypodermic needle forced into said cavity and to thereby frictionally retain said hypodermic needle within the shank prior to breaking the needle from its mount.

5. A hypodermic syringe in accordance with claim 2 wherein the wall of said elongated cavity is shaped to frictionally engage the broken needle and to retain said needle in said cavity.

6. A hypodermic syringe in accordance with claim 1 wherein said needle is scored to define a breakage point near the end of said cylinder at a location such that, when the needle is fully inserted into said cavity and the end of said cylinder is adjacent said increased diameter portion of said shank of said piston means, the needle may be predeterminately broken where it is scored by grasping said syringe cylinder in one hand and the piston means in the other hand and pivoting the two so as to provide a bending moment to the needle where it enters said cavity.

* * * * *